US006953863B2

(12) United States Patent
Pratt et al.

(10) Patent No.: US 6,953,863 B2
(45) Date of Patent: Oct. 11, 2005

(54) ALCOHOL AND GLYCOL MODIFIED ALUMINUM TRI-ALKOXIDE COMPLEXES

(75) Inventors: Charles E. Pratt, Bethlehem, PA (US); Gregory E. Kowalczyk, Nazareth, PA (US)

(73) Assignee: FedChem L.L.C., Cleveland, OH (US)

( * ) Notice: Subject to any disclaimer, the term of this patent is extended or adjusted under 35 U.S.C. 154(b) by 429 days.

(21) Appl. No.: 10/352,791

(22) Filed: Jan. 28, 2003

(65) Prior Publication Data

US 2003/0158434 A1 Aug. 21, 2003

Related U.S. Application Data

(60) Provisional application No. 60/352,337, filed on Jan. 28, 2002.

(51) Int. Cl.$^7$ .................................................. C07F 5/06
(52) U.S. Cl. .......................... 556/182; 556/181; 106/20; 106/308 Q; 252/35
(58) Field of Search ................................. 556/182, 181; 106/20, 308 Q; 252/35

(56) References Cited

U.S. PATENT DOCUMENTS

| | | | |
|---|---|---|---|
| 3,006,941 A | 10/1961 | Mudrak et al. |
| 3,198,332 A | 8/1965 | Davison |
| 3,352,895 A | 11/1967 | Holbert et al. |
| 3,686,249 A | 8/1972 | Hartmann et al. |
| 4,265,975 A | 5/1981 | Pratt |
| 4,280,917 A | 7/1981 | Pratt |
| 4,303,538 A | 12/1981 | Pratt et al. |
| 4,312,769 A | 1/1982 | Pratt |
| 4,324,670 A | 4/1982 | Pratt |
| 4,525,307 A | 6/1985 | Pratt et al. |
| 4,557,842 A | 12/1985 | Pratt et al. |
| 6,465,556 B1 | 10/2002 | Pratt et al. |

FOREIGN PATENT DOCUMENTS

EP 772144 4/1957

OTHER PUBLICATIONS

International Search Report dated Sep. 3, 2003.

*Primary Examiner*—Elvis O. Price
(74) *Attorney, Agent, or Firm*—Calfee, Halter & Griswold LLP

(57) ABSTRACT

Disclosed is an aluminum tri-alkoxide compound represented by Formula I:

$$Al(X)_a(Y)_b \qquad (I)$$

wherein "X" is an alkoxide moiety of one or more normal or iso-monohydroxy alcohols having from about 6 to 14 carbon atoms, and "Y" is an alkoxide moiety of one or more glycols having from about 6 to 8 carbon atoms. For those aluminum tri-alkoxides that comprise alkoxide moieties of alcohols having 6 or 7 carbon atoms, "a" is 0.1 to 0.75 moles and "b" is 1.45 to 1.125 moles. For those aluminum tri-alkoxides comprising alkoxide moieties of alcohols having 8 to 14 carbon atoms, "a" is 0.25 to 0.85 and "b" is 1.45 to 1.075. Further disclosed is a solution having the aluminum tri-alkoxide and a solvent. Still further disclosed is a process for making a printing ink vehicle.

13 Claims, No Drawings

ALCOHOL AND GLYCOL MODIFIED ALUMINUM TRI-ALKOXIDE COMPLEXES

CROSS REFERENCE TO RELATED APPLICATION

This application claims priority to U.S. Provisional application No. 60/352,337, filed on Jan. 28, 2002, the disclosure of which is incorporated herein in its entirety.

FIELD OF THE INVENTION

The present invention relates to modified aluminum tri-alkoxides comprising alkoxide moieties of glycols having from 6 to 8 carbon atoms and alcohols having from 6 to 14 carbon atoms. The present invention further relates to the use of such modified aluminum tri-alkoxides as rheology modifiers in printing ink vehicles.

BACKGROUND OF THE INVENTION

It is well known in the art that aluminum alkoxide structures are very complex. Aluminum alkoxides having the structural formula

STRUCTURE A

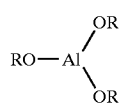

are referred to as aluminum tri-alkoxides and are useful components of products where tri-functionally (i.e. three reactive sites) is desired. The monomeric structure, i.e., Structure A, is used herein for ease of identification, although in actual occurrence there may be two, three, four or more of these aluminum tri-alkoxide molecules joined together by intermolecular forces to form corresponding dimeric, trimeric, tetrameric, or higher polymeric forms of such compounds. Whether the aluminum tri-alkoxide is in the monomeric, dimeric, trimeric, tetrameric, or higher polymeric form, it is always referred to as tri-functional because there are three reactive OR groups per atom of aluminum.

Aluminum tri-alkoxides react with carboxylic acids, carboxylic acid anhydrides, and hydroxyl groups and carboxyl groups present in other compounds. Hence, the usefulness of aluminum tri-alkoxides has been well established. For example, aluminum tri-alkoxide compounds may be used to prepare aluminum complex greases and soaps.

Aluminum tri-alkoxides, particularly aluminum tri-isopropoxide and aluminum tri-secondary butoxide, are also employed commercially in the manufacture of printing ink vehicles. The aluminum tri-alkoxides react with resins in the printing ink vehicles to modify the rheology of the vehicles. Printing ink vehicles that have been made and modified rehologically with aluminum tri-alkoxides are subsequently combined with color dispersions or pigments and solvents to produce the final printing ink. Printing inks made with vehicles comprising aluminum tri-alkoxides exhibit improved performance on high-speed printing presses.

Aluminum tri-isopropoxide is commercially available only in the form of a solid tetramer. The solid form of aluminum tri-isopropoxide is reactive with atmospheric moisture, which greatly reduces its reactivity with other reactive groups. Moreover, aluminum tri-isopropoxide, typically, is sold as a finely divided powder. The high surface area of the powder increases the likelihood of moisture contact, thereby reducing the activity and usefulness of aluminum tri-isopropoxide. Also, the solid tetrameric form of aluminum tri-isopropoxide has poor solubility in aliphatic solvents such as ink oils and is, in many cases, soluble only at elevated temperatures.

A problem with using aluminum tri-isopropoxide for rheology control in printing ink vehicles is that this aluminum tri-alkoxide releases isopropyl alcohol as a byproduct of the thickening reaction that occurs during manufacture of the printing ink vehicle. The alcohol boils up during the thickening reaction and must be condensed or scrubbed out of overhead streams to prevent it from discharging into the atmosphere. Resulting condensates and scrubbing solutions must be disposed of as hazardous waste.

Aluminum tri-secondary butoxide remains liquid in storage at ambient temperatures and is often used in place of aluminum tri-isopropoxide where a tri-functional aluminum alkoxide is desired. However, aluminum tri-secondary butoxide presents its own environmental and industrial hygiene problems. Aluminum tri-secondary butoxide typically exhibits a flash point below 100° F., which renders this aluminum tri-alkoxide subject to special handling and labeling regulations. Many manufacturers of products that include aluminum tri-alkoxides are located in areas where materials subject to such special regulations are either prohibited or subject to higher insurance premiums.

A problem with using aluminum tri-secondary butoxide in printing ink vehicles and aluminum greases is that secondary butyl alcohol is released when this aluminum tri-alkoxide is used during the manufacture of these products. Disposal of this by-product is subject to strict regulations.

U.S. Pat. No. 4,525,307 relates to a process for making modified aluminum tri-alkoxides. A higher alcohol is substituted for isopropyl alcohol in molar amounts of 0.5 or less. The modified aluminum tri-alkoxides are disclosed as having improved stability, solubility in hydrocarbon solvents and flash point compared to unmodified aluminum isopropoxide while retaining high reactivity. However, these modified aluminum tri-alkoxides still release byproduct isopropyl alcohol when used in the manufacture of printing ink vehicles.

Thus, it would be desirable to have additional aluminum tri-alkoxides that have a high aluminum content and exhibit good solubility in hydrocarbon solvents. It would also be desirable to have aluminum tri-alkoxides that exhibit high flash points. Alumunim tri-alkoxides that exhibit excellent reactivity with resins in printing ink vehicles and that do not evolve volatile alcohol byproducts during the manufacture of printing ink vehicles or aluminum complex greases are especially desirable.

SUMMARY OF THE INVENTION

The present invention provides an aluminum tri-alkoxide compound represented by Formula I:

$$Al(X)_a(Y)_b \quad (I)$$

wherein Al is an aluminum atom, "X" is an alkoxide moiety of one or more normal or iso-monohydroxy alcohols having from about 6 to 14 carbon atoms, and "Y" is an alkoxide moiety of one or more glycols having from about 6 to 8 carbon atoms. For those aluminum tri-alkoxides that comprise alkoxide moieties of one or more alcohols which have 6 to 7 carbon atoms only, "a" is 0.1 to 0.75 moles and "b" is 1.45 to 1.125 moles. For those aluminum tri-alkoxides comprising alkoxide moieties of one or more alcohols which have 8 to 14 carbon atoms only, "a" is 0.25 to 0.85 and "b" is 1.45 to 1.075. For those aluminum tri-alkoxides comprising alkoxide moieties of one or more alcohols having 6 to 7 carbon atoms and one or more alcohols having 8 to 14 carbon atoms, "a" is 0.25 to 0.85 and "b" is 1.45 to 1.075.

Aluminum tri-alkoxides that comprise molar ratios of the alcohol and glycol alkoxide moieties disclosed herein have good solubility in organic solvents such as hydrocarbon solvents and napthenic solvents. Thus, the aluminum tri-alkoxides of the present invention can be used to prepare organic solutions with a high concentration of aluminum atoms. The aluminum tri-alkoxides of the present invention have flash points that are greater than 142° F. In addition, the aluminum tri-alkoxides of the present invention do not evolve volatile byproduct alcohols when reacted with resins during the manufacture of printing ink vehicles.

The present invention also relates to solutions comprising the aluminum tri-alkoxides of the present invention and an organic solvent. Preferably, the organic solvent is selected from the group consisting of a hydrocarbon oil, a napthenic oil, a vegetable oil and a liquid ester, or combinations thereof. Such solutions are useful for preparing printing ink vehicles, aluminum complex greases, and aluminum complex soaps. The present invention also relates to methods of preparing a printing ink vehicle by reacting an aluminum tri-alkoxide of the present invention with a resin having carboxyl groups, hydroxyl groups, or both carboxyl groups and hydroxyl groups.

DETAILED DESCRIPTION OF THE INVENTION

The present invention is based, at least in part, on applicants discovery that aluminum tri-alkoxide compounds that are readily soluble in hydrocarbon and naphthenic solvents could be produced by replacing the isopropoxide moieties of aluminum tri-isoporoxide or the secondary butoxide moieties of aluminum tri-secondary butoxide with certain molar ratios of monohydroxy alcohol having from 6 to 14 carbon atoms and glycol alkoxide moieties having from 6 to 8 carbon atoms.

The aluminum tri-alkoxides of the present invention are represented by Formula I:

$$Al(X)_a(Y)_b \quad (I)$$

wherein Al is an aluminum atom, "X" is an alkoxide moiety of one or more normal or iso-monohydroxy alcohols having from about 6 to 14 carbon atoms, and "Y" is an alkoxide moiety of one or more glycols having from about 6 to 8 carbon atoms. For those aluminum tri-alkoxides that comprise alcohols having from about 6 to 7 carbon atoms, "a" is 0.1 to 0.75 moles and "b" is 1.45 to 1.125 moles. For those aluminum tri-alkoxides comprising alcohols having 8 to 14 carbon atoms, "a" is 0.25 to 0.85 and "b" is 1.45 to 1.075. For those aluminum tri-alkoxides comprising alkoxide moieties of one or more alcohols having 6 to 7 carbon atoms and one or more alcohols having 8 to 14 carbon atoms, "a" is 0.25 to 0.85 and "b" is 1.45 to 1.075. Preferably, all the valence positions on the aluminum atoms in the present aluminum tri-oxides are occupied by moieties from either normal or iso-monohydroxy alcohols having from 6 to 14 carbon atoms or glycols having from 6 to 8 carbon atoms. The molar range of aluminum to glycol disclosed herein allows for some of the compounds of the present invention to have one hydroxyl group of a glycol molecule bonded to an aluminum atom and the other hydroxyl group free and unreacted.

Suitable normal and iso-monohydroxy alcohols include, but are not limited to, the following: n-hexyl, isohexyl, 2-ethylhexyl, n-heptyl, isoheptyl, n-octyl, isooctyl, n-nonyl, isononyl, n-decyl, isodecyl, tridecyl, n-undecyl, isoundecyl, n-dodecyl, and isodecyl.

Suitable glycols include, but are not limited to the following: hexylene glycol, heptylene glycol, octylene glycol, 2,2,4-trimethyl-1,3-pentanediol (TMPD), and dipropylene glycol.

The mole ratios of the mononhydroxy alcohol alkoxide moieties and the glycol alkoxide moieties set forth above provide aluminum tri-alkoxides that are stable in hydrocarbon solutions for six months or even a year. Aluminum tri-alkoxides with glycol and alcohol alkoxide moities that fall outside the present molar ratios are not stable in hydrocarbon solutions, i.e., the aluminum tri-alkoxide solids either precipitate out of such solutions or the solutions turn into a solid mass upon standing for extended periods of time. The aluminum tri-alkoxides of the present invention have high flash points without generation of byproduct volatile alcohols in end uses. The aluminium tri-alkoxides of the present invention also have excellent low temperature reactivity. Thus, the aluminum tri-alkoxides of the present invention can either be reacted with compounds that comprise hydroxyl and carboxyl groups at lower temperatures than are normally used for such reactions or for shorter periods of time than are normally used for such reactions The following structures, denoted as Formulas (II), (III), and (IV), are hypothetical representations of aluminum tri-alkoxides having different molar ratios of aluminum, alcohol alkoxide moieties, and glycol alkoxide moieties.

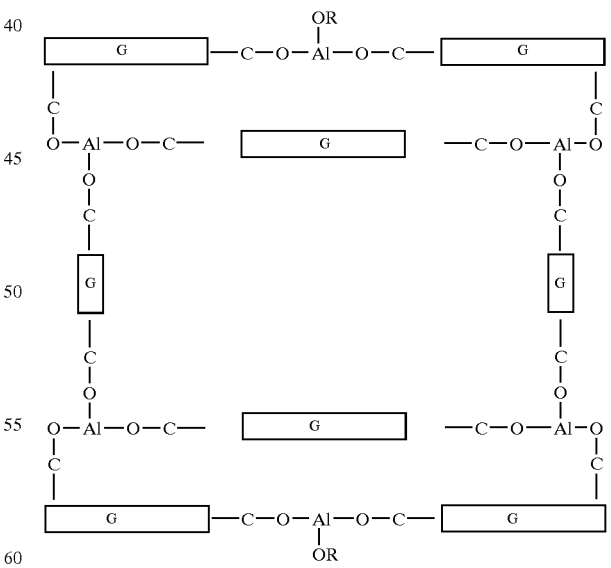

Formula (II) has a molar ratio Al/OR/G equal to 1.0/0.33/1.33. "OR" is a normal or iso-monohydroxy alcohol moiety having 6 to 14 carbon atoms. "G" is a glycol moiety having from 6 to 8 carbon atoms.

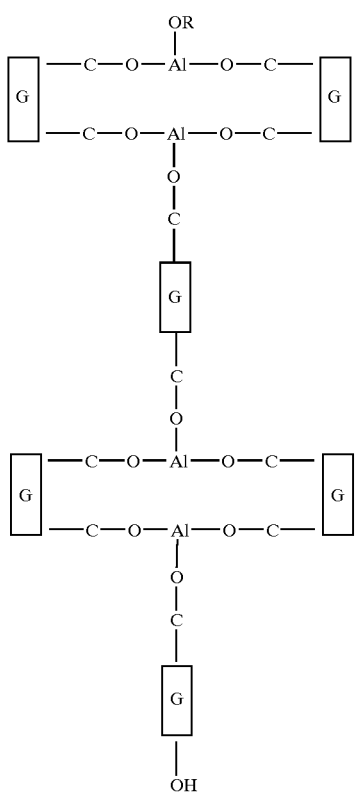

(III)

Formula (III) has a molar ratio Al/OR/G equal to 1.0/0.25/1.5. "OR" and "G" are as described above.

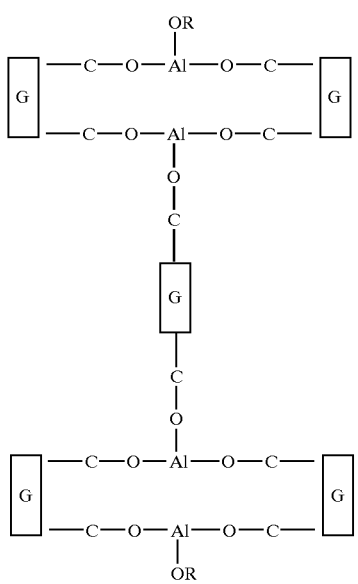

(IV)

Formula (IV) has a molar ratio Al/OR/G equal to 1.0/0.5/1.25. "OR" and "G" are as described above.

Advantageously, the present aluminum tri-alkoxides may be stored in a solution comprising an organic solvent. Useful solvents for such solutions include, but are not limited to, hydrocarbon oils, napthenic oil, vegetable oils, liquid esters, and the like.

The aluminum tri-alkoxides of the present invention may be prepared by reacting aluminum tri-isopropoxide or aluminum tri-secondary butoxide with the alcohols and glycols described above, either sequentially or in bulk. Typically, the aluminum tri-isopropoxide (or butoxide) is placed in a flask and the monohydroxy modifying alcohols and glycols are added. Then the temperature is raised to from about 70° C. to about 140° C. Vacuum is usually applied to strip off all of the remaining volatile lower alcohol if a high flash point is desired.

Preparation of Printing Ink Vehicles with Aluminum Tri-alkoxides

The use of aluminum isopropoxide and other aluminum tri-alkoxides in the manufacture of lithographic printing inks is well known. Aluminum tri-alkoxides are reactive with hydroxyl groups, carboxyl groups and with water. When added to a mixture of resins during the manufacture of printing ink vehicles (varnishes), the alkoxide sites on the aluminum react with the carboxyl and/or hydroxyl groups present on the resins in the mixture to form both covalent and coordination bonds. Resins that are typically used in printing ink vehicles include phenolic modified rosin esters, modified hydrocarbon resins, and alkyd resins. As a result of the reaction between the aluminum alkoxide and resin, a non-Newtonian viscosity increase of the printing ink vehicle is achieved. Aluminum derivatives used to increase viscosity are referred to as "gelling agents" or "gellants" in the art. Rheological modification of printing ink vehicles is very desirable because it allows faster press speeds with less misting of the ink and more perfectly formed "dots" of ink transferred to the paper. If a magnifying glass is used to examine a substrate that has been printed by lithography, it will show that the printing is actually composed of many very small dots, rather than a continuous ink film.

The present aluminum tri-alkoxides are typically employed in printing ink vehicle formulations at from about 0.2 wt % to about 5 wt % and most typically from about 0.5 wt % to about 2.0 wt %.

Preparation of Aluminum Complex Greases and Soaps with Aluminum Tri-alkoxides

Aluminum complex greases are made by an in situ reaction of an aluminum tri-alkoxide of the present invention with a mixture of an aliphatic acid having from 8 to 40 carbon atoms and an aromatic acid having from 7 to 28 carbon atoms in a lubricating oil. Representative reaction conditions are set forth at column 5, lines 19 to 40, of U.S. Pat. No. 4,557,842. Such conditions are incorporated herein by reference. Typically, the molar ratio of aromatic to aliphatic acids is between 0.2:1 and 1.5:1 and preferably from 0.5:1 to 1:1. Preferred aliphatic acids have from 18 to 24 carbon atoms. Preferred oils include, but are not limited to, hydrocarbon oils, mineral oils, vegetable oils, ester-type oils, liquid esters of phosphorous acids, alkylene polymers, and polysiloxanes.

Methods for manufacturing aluminum complex soaps from aluminum tri-alkoxides are disclosed, for example, in U.S. Pat. Nos. 3,345,291; 3,843,528; and 4,557,842. Such methods are incorporated herein by reference.

EXAMPLES

The following are non-limiting examples of the present invention. Unless otherwise indicated, all percentages and part are by weight.

Example 1

1.0 AIP/0.35 Isooctyl Alcohol/1.325 Hexylene glycol

A three-neck 1000 ml flask fitted with a mechanical stirrer and heating mantel was charged with 306.3 grams of aluminum tri-isopropoxide. 68.4 grams of isooctyl alcohol was charged to the flask followed by 234.9 grams of hexylene glycol. The mixture was heated with agitation to a temperature of 85° C. to 90° C. where isopropyl alcohol began to distill off. A high boiling petroleum solvent was added and the material was heated to 125° C. where vacuum was applied to remove the remaining isopropyl alcohol. The material was cooled to room temperature and adjusted to a final active solids content by addition of more petroleum solvent. The material is a 68% solution of the aluminum tri-alkoxide complex in petroleum solvent.

The aluminum tri-alkoxide solution was found to have a viscosity less than 400 cps and a flash point of 167° F. The aluminum content of the solution is 8%. The aluminum tri-alkoxide solution remained stable and mobile for at least one year.

Example 2
1.0 AIP/0.25 Tridecyl Alcohol/1.375 Hexylene glycol

With the apparatus of Example 1, 204.2 grams of aluminum tri-isopropoxide was added along with 50.1 grams of tridecyl alcohol and 162.7 grams hexylene glycol. The mixture was heated with agitation to 90° C. where isopropyl alcohol began to distill off. A high boiling petroleum solvent was added and the material was heated to 125° C. where vacuum was applied to remove the remaining isopropyl alcohol. The material was cooled to room temperature and adjusted to an active solids content of 71 wt % with petroleum solvent.

The aluminum tri-alkoxide solution was found to have a viscosity of less than 500 cps and a flash point of 174° F. The percent aluminum content of the solution was 8%. The solution remained clear and mobile for at least one year.

Example 3
1.0 AIP/0.35 Isooctyl Alcohol/1.325 TMPD

With the apparatus of Example 1, 408.4 grams of aluminum tri-isopropoxide was charged, followed by 91.6 grams of isooctyl alcohol and 389.2 grams of 2,2,4-trimethyl-1,3-pentanediol (TMPD). The mixture was heated to 90° C. where isopropyl alcohol began to distill off. A high boiling petroleum solvent was added and the mixture was heated to 125° C. where vacuum was applied to remove the remaining isopropyl alcohol. The solution was cooled and adjusted to a final active solids content of 49 wt % with petroleum solvent.

The aluminum tri-alkoxide solution was found to have a viscosity less than 100 cps and a flash point of 168° F. The percent aluminum content of the solution is 5%. The solution remained stable for at least one year.

Example 4
1.0 AIP/0.35 Isooctyl alcohol/1.325 Dipropylene glycol

To the apparatus of Example 1, 173.6 grams of aluminum tri-isopropoxide was charged, followed by 38.7 grams of isooctyl alcohol and 150.9 grams of dipropylene glycol. The material was heated with agitation to 90° C. where isopropyl alcohol began to distill off. A high boiling naphthenic solvent was added and the material was heated to 140° C. where vacuum was applied to remove the remaining isopropyl alcohol. The reaction mixture was cooled and adjusted to an active solids content of 46 wt % with naphthenic solvent.

The aluminum tri-alkoxoide solution was found to have a viscosity of less than 400 cps and a flash point greater than 220° F. The percent aluminum content of the solution was 5%. The solution remained clear and mobile for at least one year.

Example 5
1.0 AIP/0.125 Hexyl Alcohol/1.4375 Hexylene glycol

With the apparatus of Example 1, 163.3 grams of aluminum tri-isopropoxide was charged, followed by 10.2 grams of hexyl alcohol and 135.9 grams of hexylene glycol. The mixture was heated with agitation to 90° C. where isopropyl alcohol began distilling off. A high boiling petroleum solvent was added and the material was heated to 125° C. where vacuum was applied to remove the remaining isopropyl alcohol. The material was cooled and adjusted to a final active solids content of 61% by addition of more petroleum solvent.

The aluminum tri-alkoxide solution is a clear solution with an aluminum content of 8.0%. The solution contains 0.125 moles of fatty alcohol per mole of aluminum and has remained stable for over one year.

Example 6
1.0 AIP/0.25 Isoocytyl Alcohol/1.375 Hexylene glycol

With the apparatus of Example 1, 210.3 grams of aluminum tri-isopropoxide was charged followed by 33.5 grams of isooctyl acohol and 167.1 grams of hexylene glycol. The material was heated with agitation to 90° C. where isopropyl alcohol began distilling off. A high boiling petroleum solvent was added and the material was heated to 125° C. where vacuum was applied to remove the remaining isopropyl alcohol. The material was cooled and adjusted to a final active solids content of 65% by addition of more petroleum solvent.

The aluminum tri-alkoxide solution was a clear solution with an aluminum content of 8.0%. The solution has a viscosity less than 400 cps and a flash point of 168° F. The solution contains 0.25 moles of fatty alcohol per mole of aluminum and has remained stable for over a year.

Example 7
1.0 AIP/0.85 Isooctyl Alcohol/1.075 Hexylene glycol

With the apparatus of Example 1, 174.2 grams aluminum tri-isopropoxide was charged, followed by 94.4 grams of isooctyl acohol and 108.4 grams of hexylene glycol. The mixture was heated with agitation to 90° C. where isopropyl alcohol began distilling off. A high boiling petroleum solvent was added and the material was heated to 125° C. where vacuum was applied to remove the remaining isopropyl alcohol. The material was cooled and adjusted to a final active solids content of 48% by addition of more petroleum solvent.

The aluminum tri-alkoxide solution was a clear solution with an aluminum content of 5.0% and a flash point of 208° F. The aluminum tri-alkoxide solution contains 0.85 moles of fatty alcohol per mole of aluminum and has remained clear and stable for over one year.

Example 8
1.0 AIP/0.35 Isooctyl Alcohol/1.425 Hexylene glycol

With the apparatus of Example 1, 172.1 grams of aluminum tri-isopropoxide were charged followed by the addition of 38.4 grams of isooctyl alcohol and 141.8 hexylene glycol. The material was heated with agitation to 90° C. where isopropyl alcohol began distilling off. A high boiling petroleum solvent was added and the material was heated to 125° C. where vacuum was applied to remove the remaining isopropyl alcohol. The material was cooled and adjusted to a final active solids content of 53% by addition of more petroleum solvent. The material is a clear solution with an aluminum content of 6.0%.

The aluminum tri-alkoxide solution has a viscosity less than 400 cps and a flash point of 158° F. The solution remained clear and stable after storage for an extended period of time.

Comparative Examples

Aluminum tri-alkoxides prepared as described above with the following molar ratios of aluminum tri-isopropoxide, monohydroxyl alcohol and glycol did not remain stable when stored in an organic solution.
1.0 AIP/0.125 Isooctyl alcohol/1.4375 Hexylene glycol
1.0 AIP/0.95 Isoocytl alcohol/1.025 Hexylene glycol
1.0 AIP/0.35 Isooctyl alcohol/1.5 Hexylene glycol
1.0 AIP/0.075 Hexyl alcohol/1.4625 Hexylene glycol Aluminum tri-alkoxide prepared as described above with no hydroxyalcohol and a molar ratio of 1.0 moles AIP to 1.5 moles hexylene glycol did not remain stable when stored for an extended period of time.

Example 9
Printing Ink Vehicle

A gelled printing ink varnish (vehicle) was prepared by adding 2 wt % of a 50:50 dilution of the aluminum tri-alkoxide solution formed in Example 1 (diluted 50 wt % with petroleum solvent) to a 100 grams base varnish comprised of phenolic modified resin (39 wt %) and alkali refined linseed oil (61 wt %). The gellant was added at 100° C. with agitation. The temperature was increased to 125° C. and held for 60 minutes. The resulting gelled varnish had a short stiff texture compared to the long stringy texture of the base varnish. Falling rod viscosity measurements with the gelled varnish gave the following data: High Shear Viscosity=360 cps, Low Shear Viscosity=7400 cps, and Yield Stress=18,500 dynes/cm². The viscosity parameters of the base varnish are High Shear Viscosity=200 cps, Low Shear Viscosity=1500 cps, and Yield Stress=3700 dynes/cm².

Example 10
Printing Ink Vehicle

A gelled printing ink varnish was prepared by adding 1.6 wt % of the aluminum tri-alkoxide solution of Example 3 to a 100 grams base varnish (described above). The gellant was added at 100° C. with agitation. The temperature was increased to 125° C. and held for 60 minutes. The falling rod viscosity data for the varnish was comparable to the previous varnish prepared at that temperature: High Shear Viscosity=370 cps, Low Shear Viscosity=8000 cps, and Yield Stress of 19000 dynes/cm². The Varnish had a short stiff texture.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An aluminum tri-alkoxide compound, represented by Formula I:

$$Al(X)_a(Y)_b \quad \text{(I)}$$

wherein Al is an aluminum atom, X is an alkoxide moiety of one or more normal or iso-monohydroxy alcohols having from about 6 to 14 carbon atoms, and Y is an alkoxide moiety of one or more glycols having from about 6 to about 8 carbon atoms;

wherein a is 0.1 to 0.75 moles and b is 1.45 to 1.125 moles when the one or more alcohols have 6 to 7 carbon atoms, and wherein a is 0.25 moles to 0.85 moles and b is 1.45 to 1.075 when the one or more alcohols have from 8 to 14 carbon atoms, and wherein a is 0.25 moles to 0.85 moles and b is 1.45 to 1.075 when one or more of the alcohols have from 6 to 7 carbon atoms and one or more of the alcohols have from 8 to 14 carbon atoms.

2. The compound of claim 1 wherein the one or more alcohols have from 6 to 7 carbon atoms and wherein a is 0.1 to 0.75 moles and b is 1.45 to 1.125.

3. The compound of claim 1 wherein the one or more alcohols have from 8 to 14 carbon atoms and wherein a is 0.25 moles to 0.85 moles and b is 1.45 to 1.075.

4. The compound of claim 1 wherein one or more of the alcohols have from 6 to 7 carbon atoms, wherein one or more of the alcohols from 8 to 14 carbon atoms, and wherein a is 0.25 moles to 0.85 moles and b is 1.45 to 1.075.

5. The compound of claim 1, wherein the one or more alcohols are selected from the group consisting of n-hexyl, isohexyl, 2-ethylhexyl, n-heptyl, isoheptyl, n-octyl, isooctyl, n-nonyl, isononyl, n-decyl, isodecyl, tridecyl, n-undecyl, isoundecyl, n-dodecyl, isododecyl.

6. The compound of claim 1, wherein the alcohols are selected from the group consisting of isooctyl, hexyl, 2-ethylhexyl and tridecyl.

7. The compound of claim 1, wherein the glycols are selected from the group consisting of hexylene glycol, heptylene glycol, octylene glycol, 2,2,4-trimethyl-1,3-pentanediol, and dipropylene glycol.

8. The compound of claim 1, wherein the glycols are selected from the group consisting of hexylene glycol, dipropylene glycol, and 2,2,4-trimethyl-1,3-pentanediol.

9. A solution comprising one or more aluminum tri-alkoxide compounds of claim 1 and an organic solvent.

10. The solution of claim 9 wherein the solvent is a hydrocarbon solvent.

11. The solution of claim 9 wherein the organic solvent is selected from the group consisting of one or more hydrocarbon oils, one or more naphthenic oils, one or more vegetable oils, and one or more liquid esters, or combinations thereof.

12. The solution of claim 8 wherein the solution remains stable for at least six months when stored at ambient temperature or 0° F.

13. The solution of claim 8, wherein the solution has a flash point greater than 142° F.

* * * * *